United States Patent
Herrington et al.

(10) Patent No.: US 6,379,363 B1
(45) Date of Patent: *Apr. 30, 2002

(54) METHOD AND APPARATUS FOR REATTACHMENT OF A CRANIAL FLAP USING A CRANIAL CLAMP

(75) Inventors: Stephen Herrington, Orange Park; Jeffrey Duncan, Jacksonville; Dennis Cirino, Jacksonville; Steven Crow, Jacksonville, all of FL (US)

(73) Assignee: Walter Lorenz Surgical, Inc., Jacksonville, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/405,245

(22) Filed: Sep. 24, 1999

(51) Int. Cl.$^7$ .............................................. A61B 17/00
(52) U.S. Cl. .............................. 606/79; 606/72; 606/73; 606/104
(58) Field of Search .............................. 606/79, 69, 72, 606/73, 104, 71, 96, 102, 80; 623/16.11, 17.19; 411/338, 339, 173, 457; 29/243.525, 243.523, 243.521

(56) References Cited

U.S. PATENT DOCUMENTS

| 276,135 | A | 4/1883 | Cooley |
| 741,747 | A | 10/1903 | Walz |
| 1,105,105 | A | 7/1914 | Sherman |
| 1,390,485 | A | 9/1921 | Bell |
| 1,510,416 | A | 9/1924 | Pietz et al. |
| 1,616,232 | A | 2/1927 | Roberts et al. |
| 2,077,804 | A | 4/1937 | Morrison |
| 2,238,238 | A | 4/1941 | Westrope |
| 2,329,471 | A | 9/1943 | King |

(List continued on next page.)

FOREIGN PATENT DOCUMENTS

| DE | 1 089 116 | 9/1960 |
| DE | 2 125 556 | 6/1972 |
| DE | 28 06 609 B1 | 7/1979 |
| DE | 296 14 293 U1 | 10/1996 |
| DE | 296 14 920 U1 | 10/1996 |
| DE | 296 14 921 U1 | 10/1996 |
| DE | 296 14 922 U1 | 10/1996 |

(List continued on next page.)

OTHER PUBLICATIONS

Neurosurgical Quality Instruments, Codman & Shurtleff, 1965, pp. 10–13.

"Internal Fixation of Small Fractures", Technique Recommended by the AAO–ASIF Group, U. Heim & K.M. Pfeiffer, ©Springer–Verlag, Berlin–Heidelberg, 1974, 1982 & 1988.

(List continued on next page.)

Primary Examiner—Pedro Philogene
(74) Attorney, Agent, or Firm—Harness, Dickey & Pierce, P.L.C.

(57) ABSTRACT

This invention relates to a set of surgical instruments for use in reattachment of a cranial flap using a cranial clamp having a base, a cap and a stem. The set of surgical instruments includes an applier instrument, a stem holder instrument and a stem cutter instrument. The applier instrument slidably receives a portion of the stem and moves the cap relative to the base. The applier instrument includes a handle, a trigger and a barrel configured as a gun-style instrument, as well as includes an engagement mechanism having a contoured surface that matingly engages a contoured surface on a portion of the stem. The stem holder instrument engages and holds a portion of the stem. The stem holder instrument includes a pair of handles and a lock mechanism that may be locked upon squeezing a pair of handles once and be opened upon squeezing the pair of handles once again. The stem cutter instrument removes a portion of the stem from the cranial clamp. The stem cutter instrument includes a capture mechanism which retains a sheared portion of the stem.

39 Claims, 13 Drawing Sheets

U.S. PATENT DOCUMENTS

| | | |
|---|---|---|
| 2,489,870 A | 11/1949 | Dzus |
| 2,494,229 A | 1/1950 | Collison |
| 2,511,051 A | 6/1950 | Dzus |
| 2,576,649 A | 11/1951 | Slind |
| 2,791,868 A | 5/1957 | Viken |
| 2,846,744 A | 8/1958 | Becker |
| 3,019,887 A | 2/1962 | Lowden |
| 3,281,171 A | 10/1966 | Hughes |
| 3,547,114 A | 12/1970 | Haboush |
| 3,712,357 A | 1/1973 | Corbett, et al. |
| 3,741,205 A | 6/1973 | Markolf et al. |
| 3,779,240 A | 12/1973 | Kondo |
| 3,790,507 A | 2/1974 | Hodosh |
| 3,875,936 A | 4/1975 | Volz |
| 4,033,243 A | 7/1977 | Kirrish et al. |
| 4,116,200 A | 9/1978 | Braun et al. |
| 4,219,015 A | 8/1980 | Steinemann |
| 4,275,490 A | 6/1981 | Bivins |
| 4,360,025 A | 11/1982 | Edwards |
| 4,503,848 A | 3/1985 | Caspar et al. |
| 4,643,610 A | 2/1987 | Bien |
| 4,651,724 A | 3/1987 | Berentey et al. |
| 4,669,473 A | 6/1987 | Richards, et al. |
| 4,683,878 A | 8/1987 | Carter |
| 4,688,561 A | 8/1987 | Reese |
| 4,793,335 A | 12/1988 | Frey et al. |
| 4,802,477 A | 2/1989 | Gabbay |
| 4,875,815 A | 10/1989 | Phillips |
| 4,903,691 A | 2/1990 | Heinl |
| 4,905,679 A | 3/1990 | Morgan |
| 4,905,680 A | 3/1990 | Tunc |
| 4,923,471 A | 5/1990 | Morgan |
| 4,988,351 A | 1/1991 | Paulos, et al. |
| 5,013,316 A | 5/1991 | Goble, et al. |
| 5,087,202 A | 2/1992 | Krenkel |
| 5,098,433 A | 3/1992 | Freedland |
| 5,139,497 A | 8/1992 | Tilghman et al. |
| 5,167,665 A | 12/1992 | McKinney |
| 5,196,016 A | 3/1993 | Buser et al. |
| 5,201,737 A | 4/1993 | Leibinger et al. |
| 5,250,049 A | 10/1993 | Michael |
| 5,268,001 A | 12/1993 | Nicholson, et al. |
| 5,269,784 A | 12/1993 | Mast |
| 5,342,393 A | 8/1994 | Stack |
| 5,346,492 A | 9/1994 | Morgan |
| 5,350,399 A | 9/1994 | Erlebacher et al. |
| 5,352,229 A | 10/1994 | Goble et al. |
| 5,372,598 A | 12/1994 | Luhr et al. |
| 5,433,053 A | 7/1995 | Tulloch |
| 5,433,719 A | 7/1995 | Pennig |
| 5,468,242 A | 11/1995 | Reisberg |
| 5,501,685 A | 3/1996 | Spetzler |
| 5,549,620 A | 8/1996 | Bremer |
| 5,578,036 A | 11/1996 | Stone et al. |
| 5,600,878 A * | 2/1997 | Byrne et al. ............ 29/243.525 |
| 5,601,558 A | 2/1997 | Torrie, et al. |
| 5,666,710 A * | 9/1997 | Weber et al. ........... 29/243.523 |
| 5,669,912 A * | 9/1997 | Spetzler ........................ 606/72 |
| 5,707,373 A * | 1/1998 | Sevrain et al. ................ 606/72 |
| 5,722,976 A | 3/1998 | Brown |
| 5,800,436 A * | 9/1998 | Lerch ............................ 606/72 |
| 5,916,200 A | 1/1999 | Eppley et al. |
| 5,928,244 A * | 7/1999 | Tovey et al. ................. 606/104 |
| 6,021,553 A * | 2/2000 | Bieber et al. ........... 29/243.521 |
| 6,068,631 A * | 5/2000 | Lerch ............................ 606/72 |

FOREIGN PATENT DOCUMENTS

| | | |
|---|---|---|
| DE | 196 038 87 A1 | 8/1997 |
| EP | 0 290 138 A2 | 4/1987 |
| EP | 0 291 632 A1 | 5/1987 |
| EP | 0 433 852 A1 | 6/1991 |
| EP | 0 510 390 A1 | 10/1992 |
| FR | 2 386 301 | 11/1978 |
| FR | 2 631 539 A1 | 5/1988 |
| JP | H05-21954 | 3/1993 |
| JP | H05-220714 | 8/1993 |
| SU | 15125874 A1 | 10/1989 |
| SU | 1600713 | 10/1990 |
| SU | 1655477 A1 | 6/1991 |
| WO | 97/01398 | 2/1997 |
| WO | 97/29708 | 8/1997 |

OTHER PUBLICATIONS

"Manual of Internal Fixation Technique", Recommended by the AO–Group, M.E. Mueller, M. Allgower, & H. Willenegger, ©Springer–Verlag, Berlin–Heidelberg, 1970.

For The Few Who Know The Difference, TiMesh Inc., (1 sheet).

Four pages from catalog of products offered by Codman & Shurtleff, undated, disclosing Burr Hole Buttons.

Translation of G 85 23 003.8 (Germany), BONE PLATE, Feb./1986, Oswald Leibinger Gmbh (Owner).

Hans G. Luhr, M.D., D.M.D., "Indications for Use of a Microsystem for Internal Fixation in Craniofacial Surgery", J. of Craniofacial Surgery, vol. 1, No. 1, Jan., 1990, pp. 35–52.

Howmedica International, Inc., "Vitallium—Verschiedene Implantate" p. 54.

Leibinger LP, "Leibinger," copyright 1995, (1 sheet).

Walter Lorenz Surgical, Inc., "Surgical Instrument Catalog 5th Edition," copyright 1993, pp. 10–11.

Walter Lorenz Surgical, Inc., 1.5/2.0mm Combination Titanium Osteosynthesis System, copyright 1994.

Aesculap CranioFIX brochure, date Mar. 1998.*

* cited by examiner

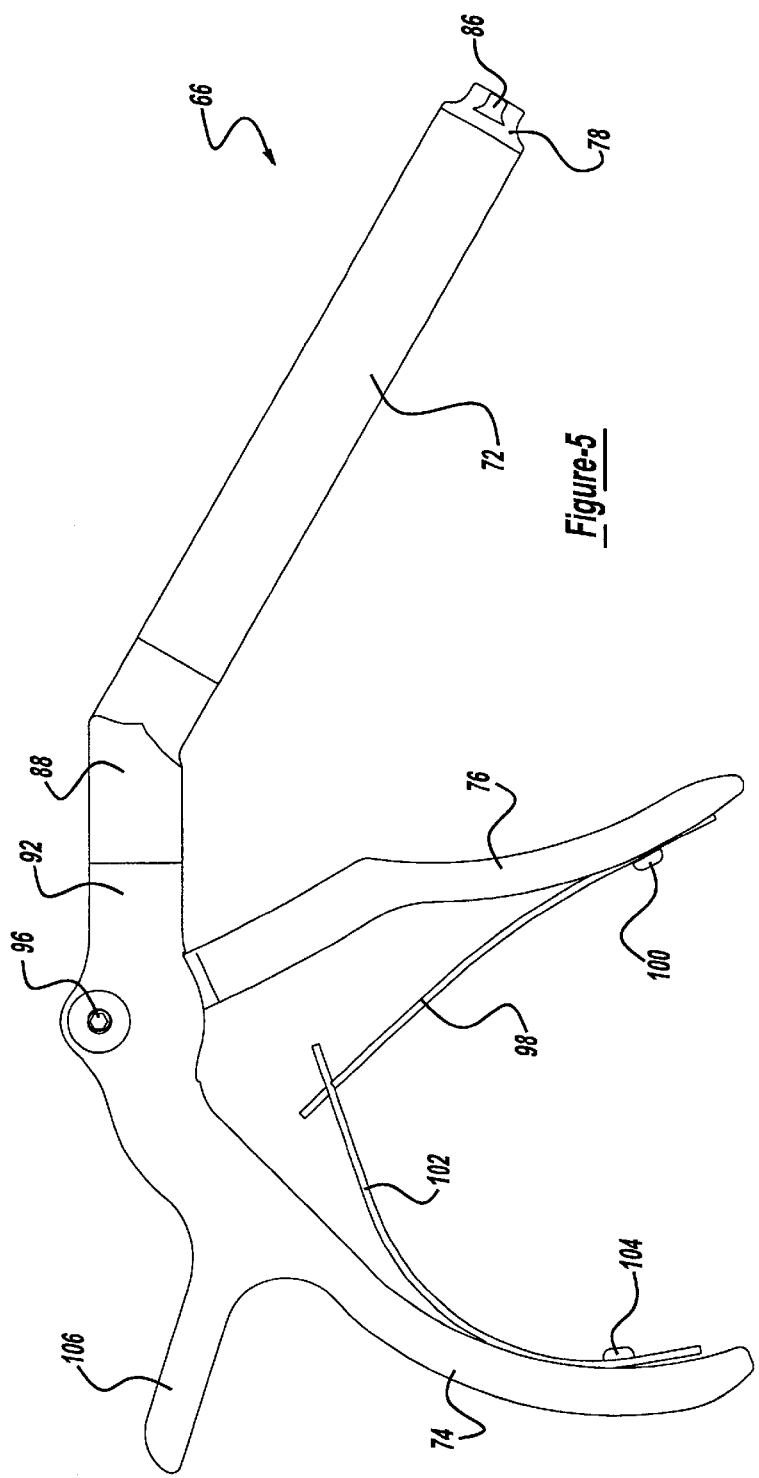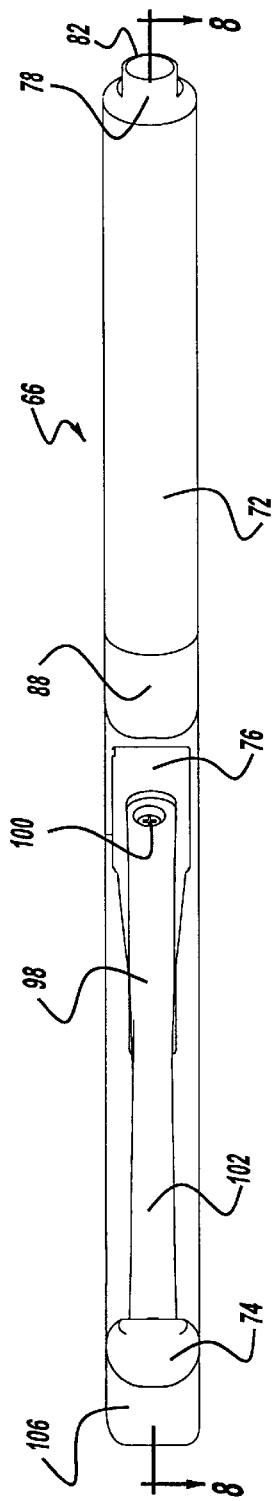

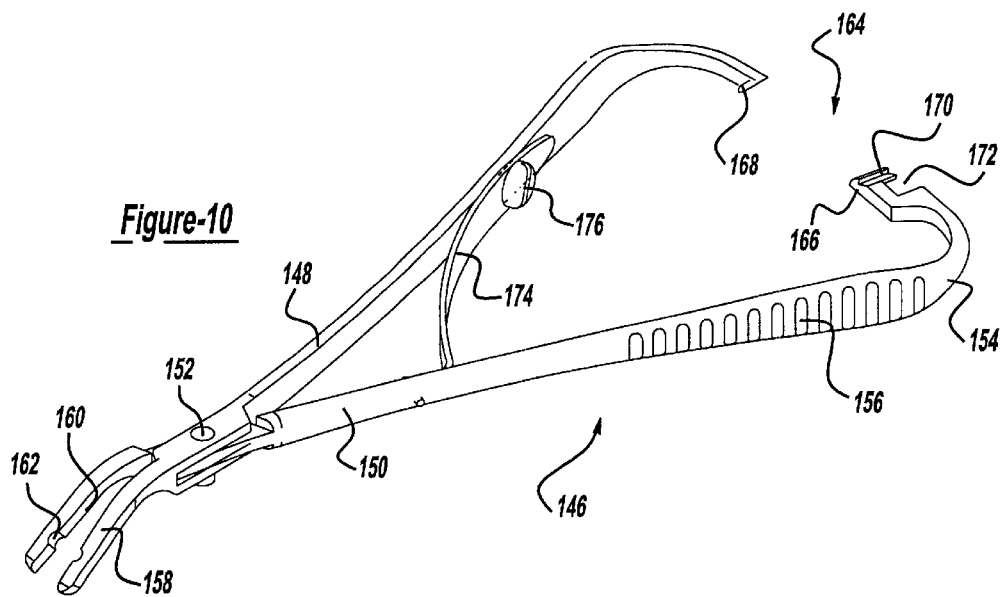
_Figure-10_
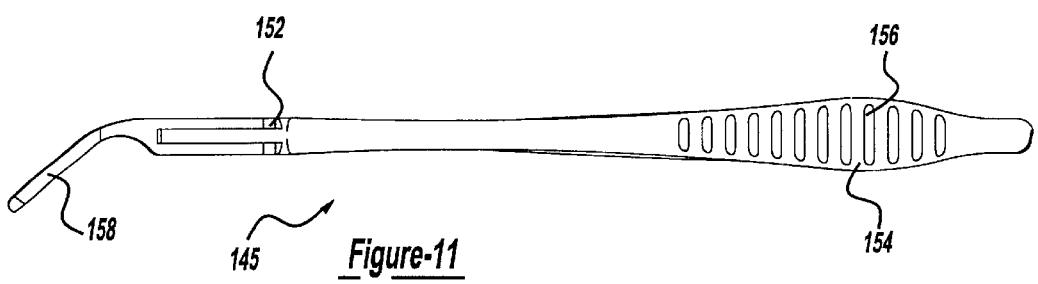
_Figure-11_
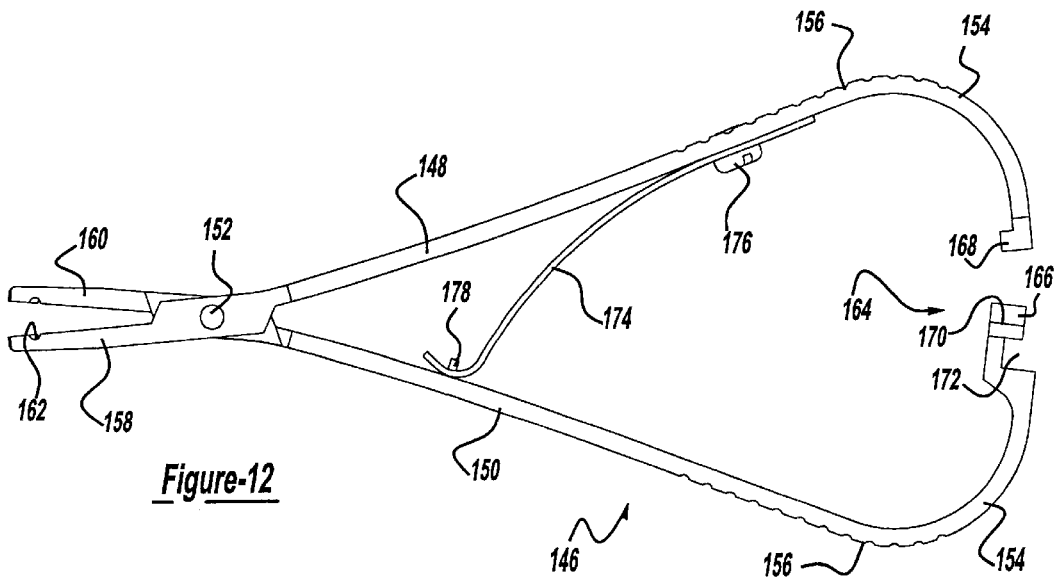
_Figure-12_

METHOD AND APPARATUS FOR REATTACHMENT OF A CRANIAL FLAP USING A CRANIAL CLAMP

BACKGROUND OF THE INVENTION

1. Field of the Invention

This invention relates generally to a method and apparatus for use in surgical procedures and, more particularly, to a method and apparatus for re-attachment of a cranial flap using a cranial clamp.

2. Discussion of the Related Art

During various types of surgical procedures, it is often necessary to remove and re-attach a portion of bone. In certain neuro-surgical procedures, this portion of bone may include a portion of a human skull. For example, when performing surgery on the brain, it is often necessary to perform a craniotomy to provide access to the brain. To perform a craniotomy, one or more holes are drilled through the skull. These holes are generally known as burr holes which may be located, for example, at the corners of a triangular region of bone that is to be temporarily removed. After the burr holes have been drilled, osteonomies are made by a saw, (i.e., a craniotome) which connect the burr holes. This type of saw will typically include a guide nose that serves to avoid injuries to the dura matter. The resulting bone cover or cranial flap is subsequently lifted or removed from the underlying dura to expose and provide access to the brain.

Once the surgical procedure on the brain is completed, the bone flap or cover must be reattached to the skull at its original position. One procedure for reattaching a bone flap involves the use of sutures to retain the bone flap relative to the skull. However, this technique may not provide a desired rigid connection between the bone flap and the skull. Other techniques employed may use mechanical clamps which engage both an inner and outer surface of the bone flap and skull to retain one relative to the other. However, some of the commercially available mechanical clamps may not provide enough holding strength to assure rigid fixation of the bone flap relative to the skull, while others are difficult to implant. For example, some techniques require the use of many individual instruments which are difficult to handle and maneuver during the surgical procedure. Some of these instruments are also designed specifically for only right or left hand use and require an excess amount of arm or grip strength to operate. Others tend to create sharp surfaces which may cause patient discomfort, while others are also difficult to assemble/disassemble for cleaning and sterilization purposes.

What is needed then is a method and apparatus for reattachment of a cranial flap using a cranial clamp which does not suffer from the above-mentioned disadvantages. This will, in turn, provide a more rigid securement of the cranial flap relative to the skull, reduce the number of surgical instruments required to implant the cranial clamp, reduce or eliminate any sharp edges created on the cranial clamp, provide a set of instruments that may be used by right or left handed users, provide instruments that may be easily assembled/disassembled for cleaning and sterilization, and provide contoured mating surfaces between the cranial clamp and an applier instrument to reduce grip strength required to implant the cranial clamp. It is, therefore, an object of the present invention to provide such a method and apparatus for reattachment of a cranial flap using a cranial clamp.

SUMMARY OF THE INVENTION

In accordance with the teachings of the present invention, a method and apparatus for reattachment of a cranial flap using a cranial clamp having a base, a cap and a stem is disclosed. This reattachment method employs a set of surgical instruments that quickly and efficiently implants the cranial clamp to retain the cranial flap. This set of surgical instruments includes an applier instrument, a stem holder instrument, a stem cutter instrument, and a removal forceps instruments. Each of these instruments has a distinct use during the implantation procedure.

In one preferred embodiment, a set of surgical instruments for use in reattachment of a cranial flap using a cranial clamp having a base, a cap, and a stem includes an applier instrument and a stem cutter instrument. The applier instrument slidably receives a portion of the stem and moves the cap relative to the base. The applier instrument includes a handle, a trigger and a barrel configured as a gun-style instrument. The stem cutter instrument removes a portion of the stem from the cranial clamp, such that each of these instruments is used to implant the cranial clamp to reattach the cranial flap.

In another preferred embodiment, a set of surgical instruments for use in reattachment of a cranial flap using a cranial clamp having a base, a cap, and a stem includes an applier instrument and a stem cutter instrument. The applier instrument slidably receives a portion of the stem and moves the cap relative to the base. The applier instrument includes an engagement mechanism having a textured engagement surface that matingly engages a textured engagement surface on a portion of the stem. The stem cutter instrument removes a portion of the stem from the cranial clamp, such that each of these instruments is used to implant the cranial clamp to reattach the cranial flap.

In yet another preferred embodiment, a set of surgical instruments for use in reattachment of a cranial flap using a cranial clamp having a base, a cap and a stem includes an applier instrument, a stem holder instrument and a stem cutter instrument. The applier instrument slidably receives a portion of the stem and moves the cap relative to the base. The stem holder instrument engages and holds a portion of the stem and includes a pair of handles and a lock mechanism that may be locked upon squeezing the pair of handles once and opened upon squeezing the pair of handles once again. The stem cutter instrument removes a portion of the stem from the cranial clamp, such that each of these instruments is used to implant the cranial clamp to reattach the cranial flap.

In yet another preferred embodiment, a set of surgical instruments for use in reattachment of a cranial flap using a cranial clamp having a base, a cap, and a stem includes an applier instrument and a stem cutter instrument. The applier instrument slidably receives a portion of the stem and moves the cap relative to the base. The stem cutter instrument removes a portion of the stem from the cranial clamp and includes a capture mechanism that retains a sheared portion of the stem, such that each of these instruments is used to implant the cranial clamp to reattach the cranial flap.

In another preferred embodiment, a method of reattachment of the cranial flap using a cranial clamp having a base, a cap and a stem is set forth. This method includes engaging a textured engagement surface on a portion of the stem with an applier instrument having a mating textured engagement surface, moving the cap relative to the base as the applier instrument matingly engages the textured engagement surface on the portion of the stem, and removing a portion of the stem from the cranial clamp with a stem cutter instrument.

Use of the present invention provides a method and apparatus for reattachment of a cranial flap using a cranial clamp. As a result, the aforementioned disadvantages associated with the currently available reattachment devices, instruments and procedures have been substantially reduced or eliminated.

BRIEF DESCRIPTION OF THE DRAWINGS

Still other advantages of the present invention will become apparent to those skilled in the art after reading the following specification and by reference to the drawings in which:

FIG. 5 is a side elevational view of the cranial clamp applier instrument of FIG. 4;

FIG. 6 is a bottom elevational view of the cranial clamp applier instrument of FIG. 4;

FIG. 10 is a perspective view of a cranial clamp post holder instrument according to the teachings of the present invention;

FIG. 11 is a top elevational view of the cranial clamp post holder instrument of FIG. 10;

FIG. 12 is a side elevational view of the cranial clamp post holder instrument of FIG. 10, shown in an opened position;

DETAILED DESCRIPTION OF THE PREFERRED EMBODIMENT(S)

The following description of the preferred embodiments concerning a method and apparatus for reattachment of a cranial flap using a cranial clamp and instruments are merely exemplary in nature and are not intended to limit the invention or its application or uses. Moreover, while the present invention is described in detail below with reference to a particular bone flap reattachment procedure, it will be appreciated by those skilled in the art that the present invention is clearly not limited to only this type of reattachment procedure and may be utilized with various other surgical procedures.

Figure 1:
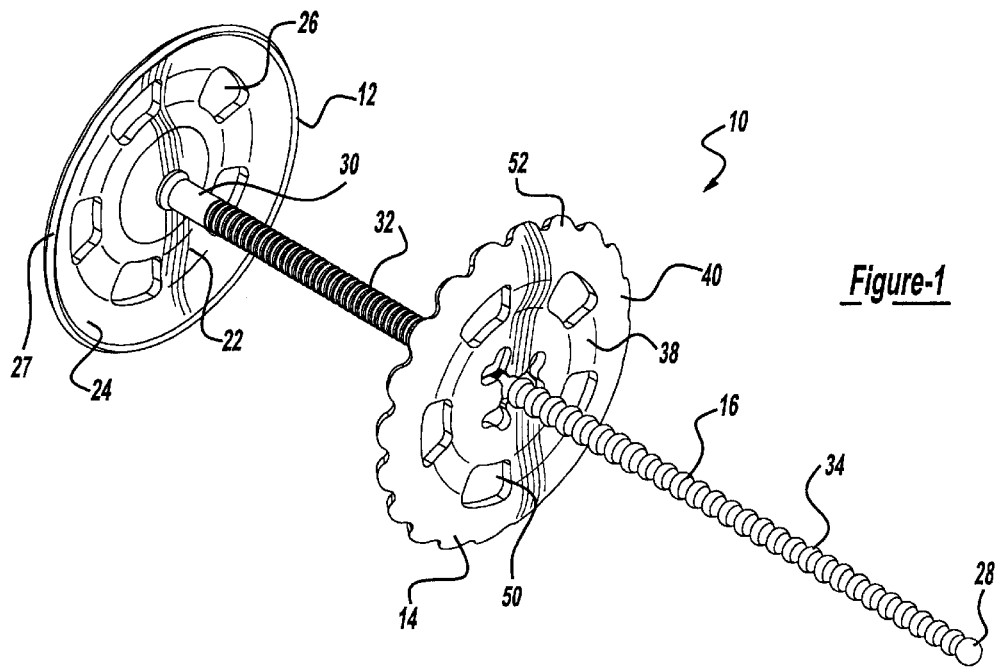
FIG. 1 is a perspective view of a cranial clamp for use in reattachment of a cranial flap according to the teachings of the present invention.
Figure 2:
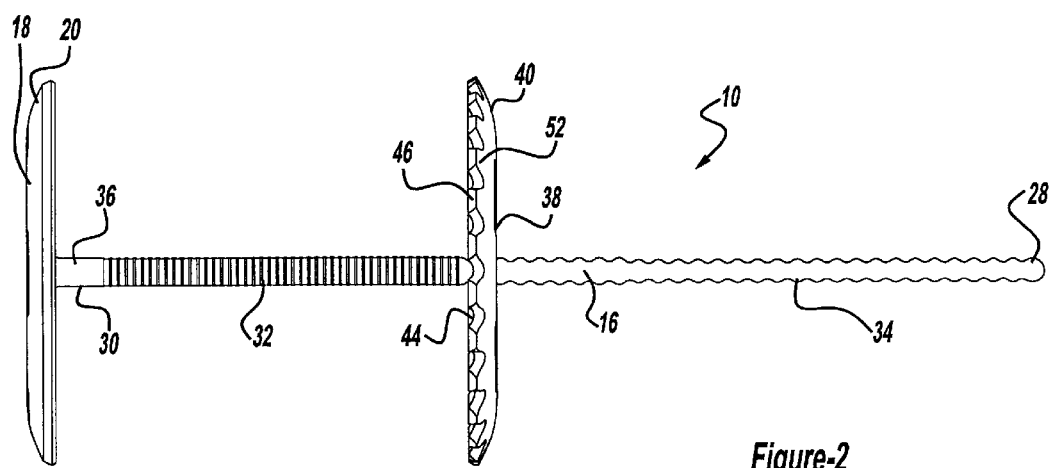
FIG. 2 is a side elevational view of the cranial clamp of FIG. 1.
Figure 3:
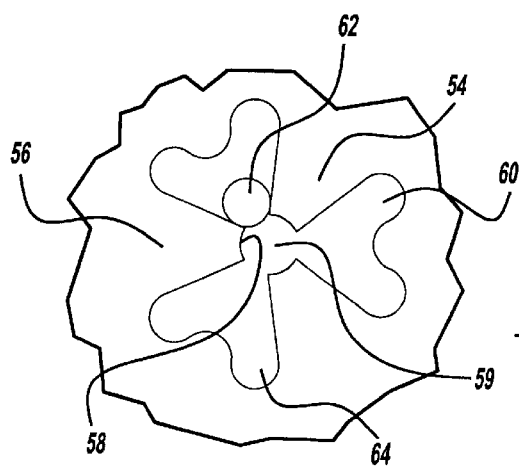
FIG. 3 is a front elevational view of resilient fingers utilized by the cranial clamp of FIG. 1.
Figure 4:
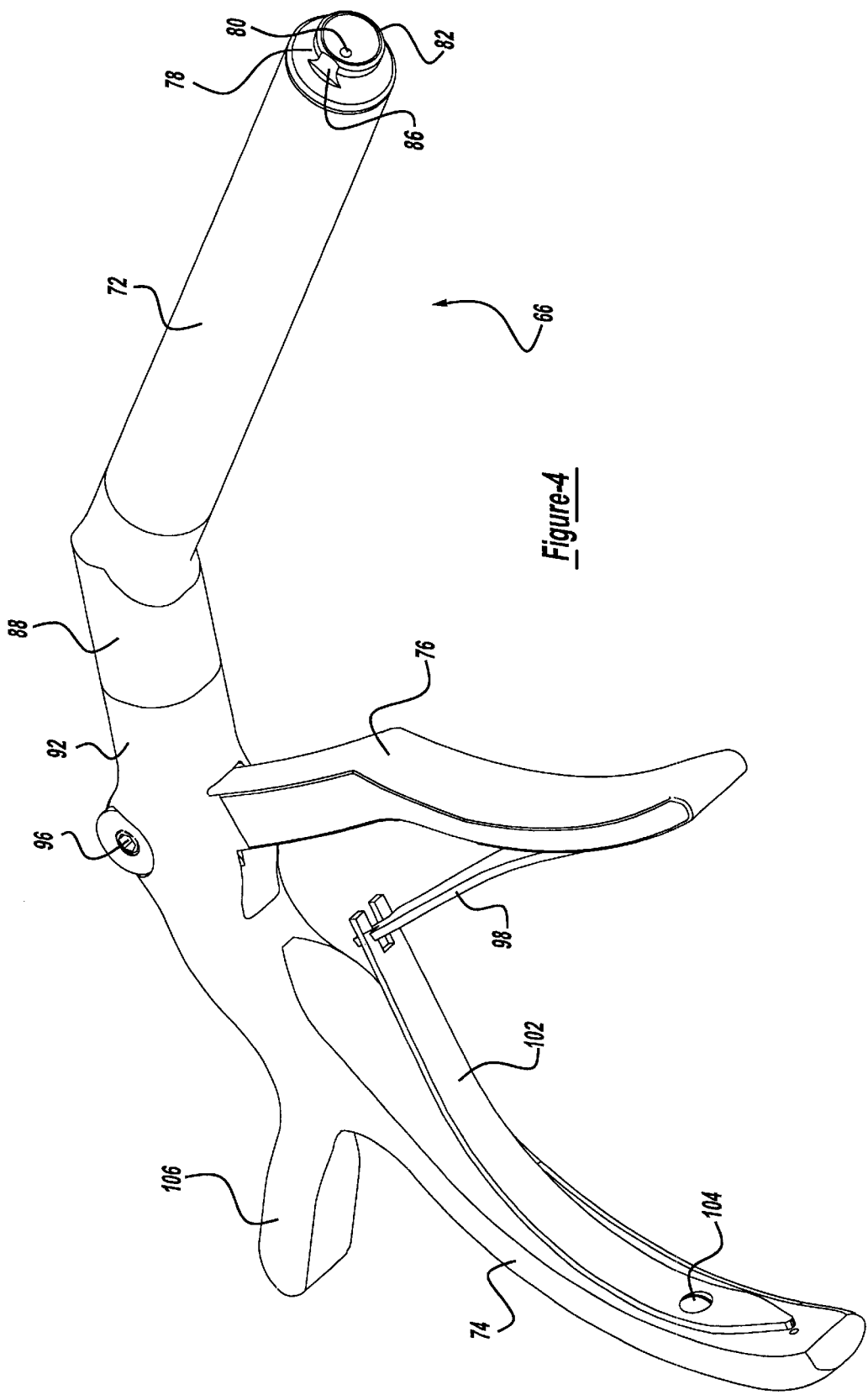
FIG. 4 is a perspective view of a cranial clamp applier instrument according to the teachings of the present invention.
Figure 7:
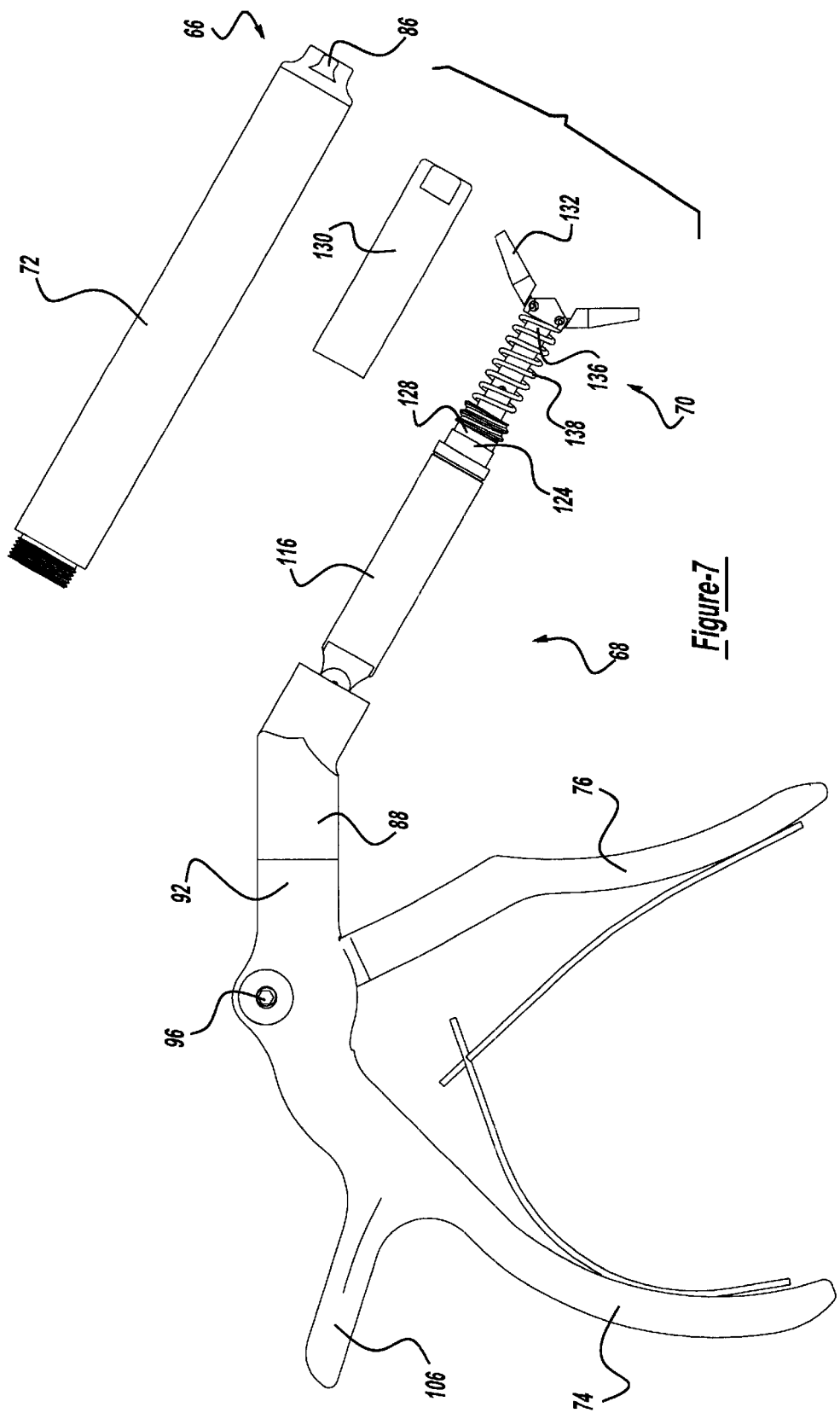
FIG. 7 is a partial exploded assembly view of the cranial clamp applier instrument of FIG. 4.

Referring to FIGS. 1–3, an adjustable cranial clamp 10 for use in rigidly securing and reattaching a cranial flap to a skull is shown. The cranial clamp 10 is preferably formed from titanium, a bio-resorbable polymer or any other appropriate biocompatible material. The cranial clamp 10 includes a disk shaped base 12, a disk shaped cap 14 and an elongated cylindrical stem 16. The base 12 includes an outer circular concave sidewall 18 and an outer annular convex sidewall 20. Correspondingly, the base 12 further includes an inner circular convex sidewall 22 and an inner annular concave sidewall 24. Passing through the sidewalls of the base 12 are a plurality of rectangularly shaped bores 26 which reduce the overall mass of the cranial clamp 10, as well as permit passage of fluid and bony ingrowth. The base 12 also includes a smooth circular ridge 27 located about the circumference of the base 12. The smooth circular ridge 27 engages the underside of the cranial flap and the skull.

The cylindrical stem 16 includes a proximal end 28 and a distal end 30. The distal end 30 of the stem 16 is integral with the base 12 and may be formed by way of a weld. Positioned between the distal end 30 and the cap 14 are a plurality of fine rectangularly-shaped annular ridges 32. These ridges 32 are snappingly engaged by the cap 14, as the cap 14 is adjustably positioned relative to the base 12, further discussed herein. Positioned between the cap 14 and the proximal end 28 are a plurality of coarse arcuately-shaped annular ridges 34 which form a textured engagement surface. This textured engagement surface nestingly mates with an applier instrument to increase the frictional engagement between the applier instrument and the stem 16 which thereby reduces the overall grip strength required by a user to move the cap 14 relative to the base 12, further discussed herein. The stem 16 further includes a smooth cylindrical portion 36 located adjacent to the base 12 which is generally positioned adjacent to the skull and the bone flap.

The cap 14 includes an outer circular concave sidewall 38 and an outer annular convex sidewall 40. Correspondingly, the cap 14 further includes an inner circular convex sidewall 44 and an inner annular concave sidewall 46. Passing through the sidewalls of the cap 14 are a plurality of rectangular shaped bores 50 which also reduces the overall mass of the adjustable cranial clamp 10, as well as permits passage of fluid and bony ingrowth. It should further be noted that both the base 12 and cap 14 may be formed with different shaped bores or without any bores whatsoever. Located about the circumference of the cap 14 are a plurality of scalloped protrusions 52 which fixedly engage or contact the outer cranial flap and skull to rigidly retain one relative to the other.

Located at the center of the cap 14 are a plurality of resilient fingers 54, shown clearly in FIG. 3. Each resilient finger 54 includes a proximal hinged region 56 and a semi-circular arcuate distal tip 58. Each semi-circular distal tip 58 is initially formed slightly offset or not circular when the cap 14 is still planar. Once the cap 14 has been contoured to have concave and convex surfaces as described above, each offset distal tip 58 forms a substantially circular engagement region 59 about the stem 16. In this regard, approximately fifty percent (50%) of contact about the stem 16 occurs which provides an improved contact area about the stem 16. This provides both increased retainment, as well as removal strength of the cap 14 relative to the stem 16.

Each resilient finger 54 is formed or defined by a plurality of heart-shaped bores 60 adjacent the center of the cap 14. The heart-shaped bores 60 are formed by use of a cutter 62 which easily and efficiently forms a pair of legs 64 within the bore 60. In this regard, each heart-shaped bore 60 is formed by use of a .038 inch cutter 62 that forms 0.020 inch openings adjacent each of the arcuate tips 58. By forming a large heart shaped bore 60 with the cutter 62 moved adjacent to, but not though the circular engagement region 59, use of the larger circular cutter 62 is possible. Moreover, by using a 0.038 inch cutter as opposed to a 0.020 inch cutter, the time and cost to form the fingers 54 is significantly reduced by as much as three times.

Referring now to FIGS. 4–9, a cranial clamp applier instrument 66 according to the teachings of the present invention is shown. The applier instrument 66 is utilized to move or compress the cap 14 relative to the base 12 to thereby clampingly engage a cranial flap relative to a skull, further discussed herein. The applier instrument 66 is formed by a combination of an outer assembly 68 and an inner assembly 70. The outer assembly 68 includes a substantially cylindrical applier tube 72, an applier handle 74 and an applier trigger 76. This outer assembly 68 forms a gun or Rongeur-style applier instrument 66 which is easier to handle and use as opposed to a plier-style applier. Moreover, this enables either right or left handed use of the applier instrument 66.

The applier tube 72 includes a threaded endcap 78 which threadably engages an inner distal end of the applier tube 72. The endcap 78 defines a substantially cylindrical bore 80 which slidably receives the stem 16 and an annular engagement ledge 82 that engages the cap 14. The endcap 78 is threadably engaged to the distal end of the applier tube 72, via internal and external threads 84 and then welded together. The endcap 78 further includes a pair of parallel opposed flat regions 86 which are operable to be engaged by a wrench for removal of the endcap 78 and the applier tube 72 from an applier gooseneck 88. The proximal end of the applier tube 72 is threadably secured to the applier gooseneck 88, via internal and external threads 90. The applier gooseneck 88 is angled downward at about thirty degrees (30°) relative to a barrel portion 92 of the applier handle 74 and secured to the barrel portion 92 by way of a slide press fit and welded together. This angle provides for a natural hand position relative to the skull when implanting the cranial clamp 10. Extending through the barrel 92, the gooseneck 88 and the tube 72 is an inner assembly shaft or bore 96 which slidably receives the inner assembly 70.

Figure 8:
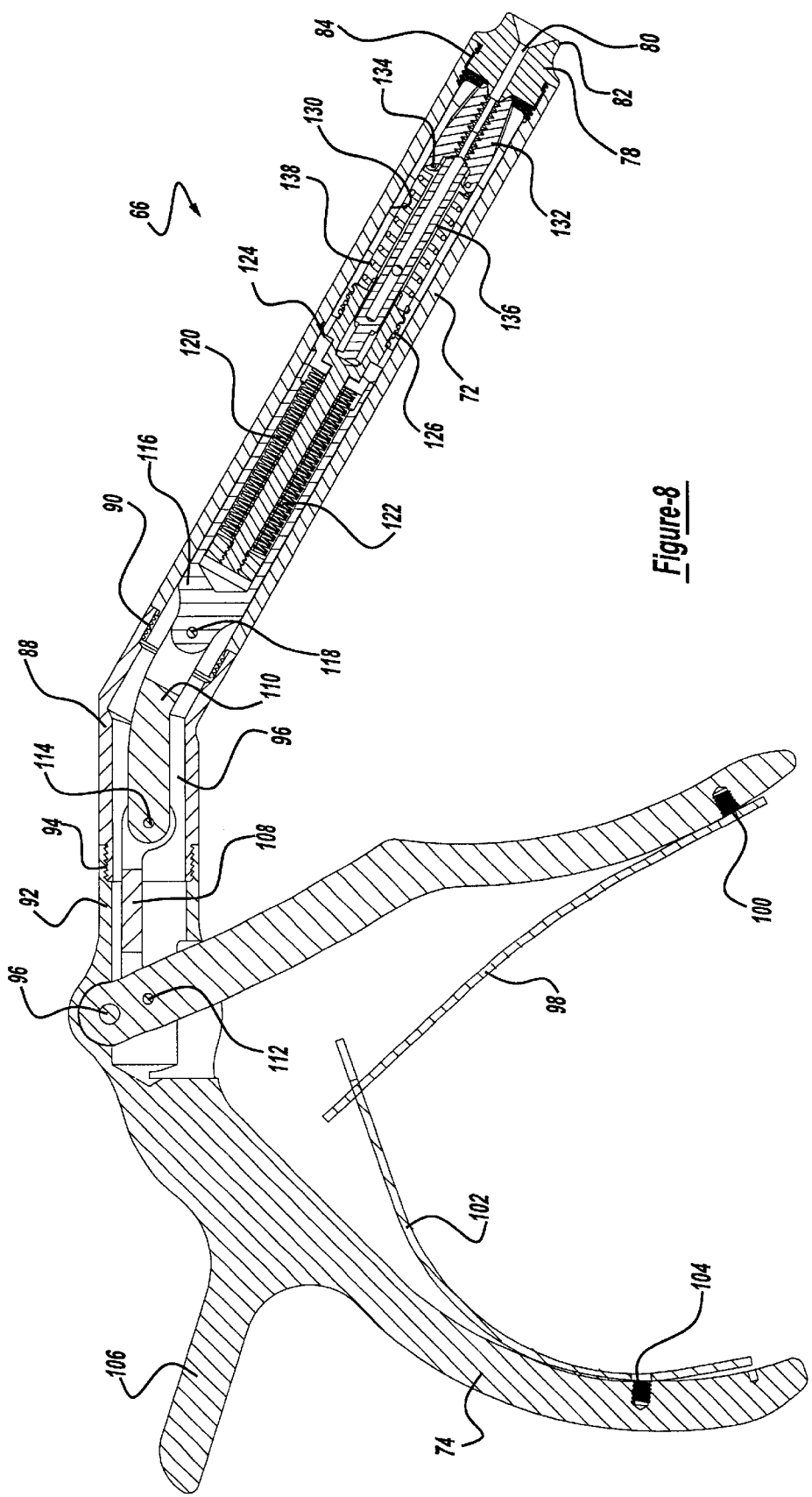
FIG. 8 is a side cross-sectional view of the cranial clamp applier instrument taken along line 8—8 of FIG. 6.

The applier trigger 76 is pivotably secured to the applier handle 74, via an applier main pivot pin 96. Secured to the trigger 76 is a front spring 98, via a threaded screw 100 and secured to the handle 76 is a rear spring 102, via a threaded screw 104. The springs 98 and 102 bias the trigger 76 outward, as shown in FIG. 8. The handle 74 is further provided with an extension 106 that prevents slippage of a user's hand during engagement of the handle 74 and trigger 76. In this regard, the handle 74 and trigger 76 may be grasped by either a right or left handed user with the extension 106 extending above the thumb of the user to inhibit the user's hand from slipping off the handle 74.

The inner assembly 70 includes a first linkage arm 108 and a second angled linkage arm 110. The first linkage arm 108 is pivotably connected to the trigger 76 at pivot point 112 and pivotably connected to the second linkage arm at pivot point 114. The second angled linkage arm 110 is pivotably connected to a Belleville washer tube 116 at pivot point 118. The Belleville washer tube 116 slidably retains or holds a plurality of stacked Belleville washers 120 which surround a cylindrical shaft 122. The stack of Belleville washers 120 preferably consists of about forty-eight (48) Belleville washers 120 to provide a safety limiting mechanism and achieve the desired stroke length. In other words, the maximum amount of compression force that may be applied to the cap 14 is limited to between about 60 lbs. to about 110 lbs. Located at the distal end of the Belleville washers 120 is a Belleville plunger 124 that is secured to the Belleville tube 116. The Belleville plunger 124 includes an external threaded sidewall portion 126 and a pair of planar parallel regions 128 that are operable to be engaged with a wrench, further discussed herein. A cylindrical collet tube 130 is threadably retained to the Belleville plunger 124, via the threaded sidewall 126. Located within the collet tube 130 is an engagement mechanism or a pair of collets 132 that pivot at pivot points 134 along collet pin 136. Positioned concentric with the collet pin 136 is a compression spring 138 which provides an axially outward or distal force upon the collets 132.

Figure 9:
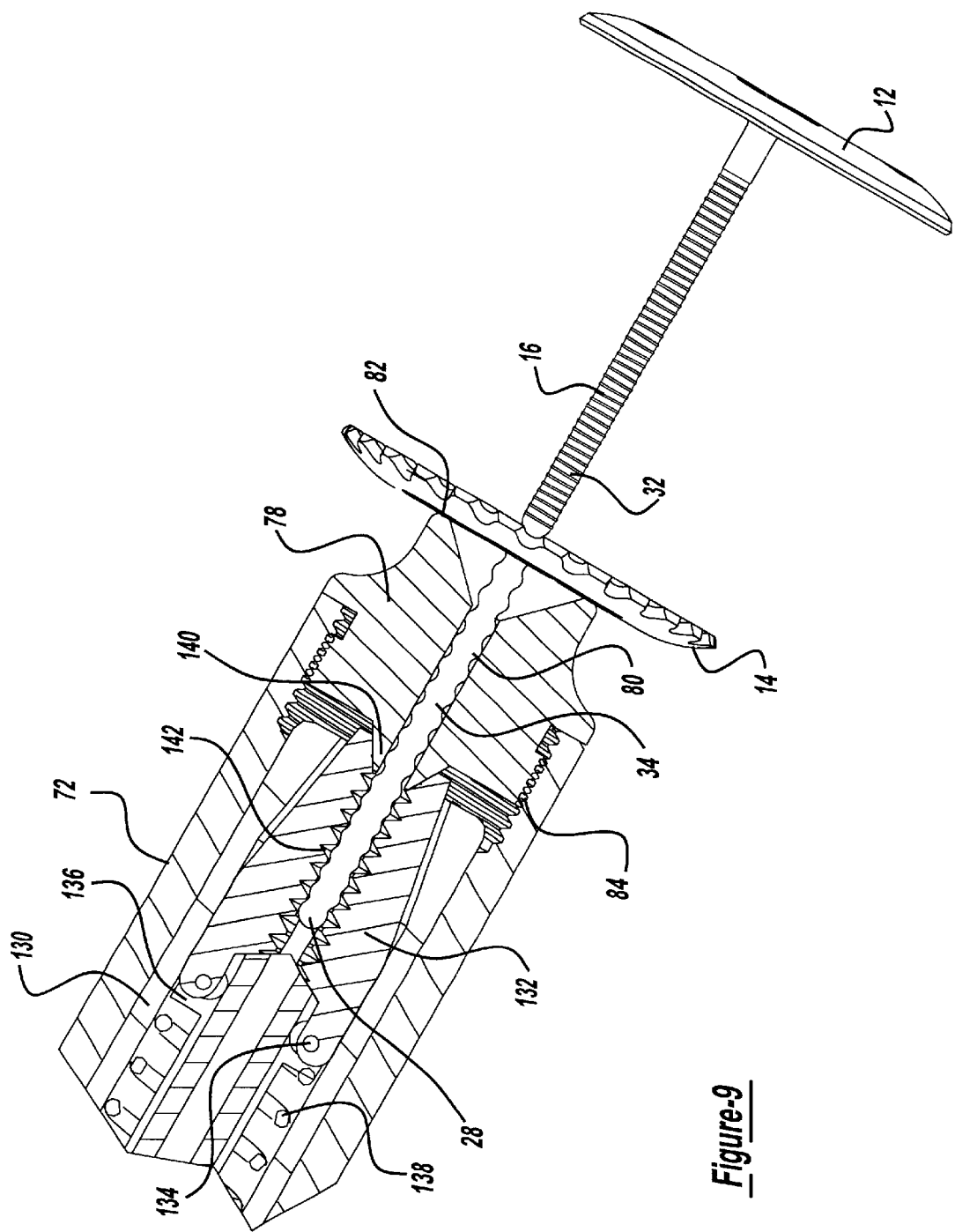
FIG. 9 is an enlarged cross-sectional view of a distal end of the cranial clamp applier instrument shown in operative association with the cranial clamp.
Figure 13:
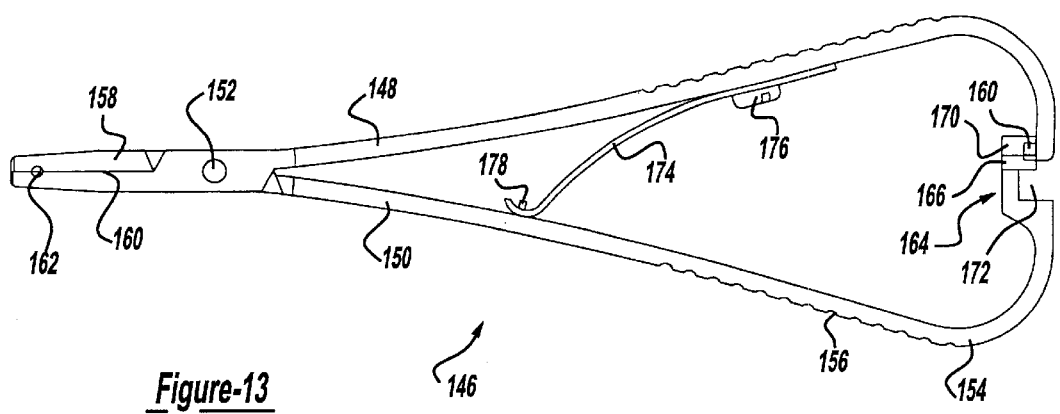
FIG. 13 is a side elevational view of the cranial clamp post holder instrument of FIG. 10, shown in a closed position.
Figure 14:
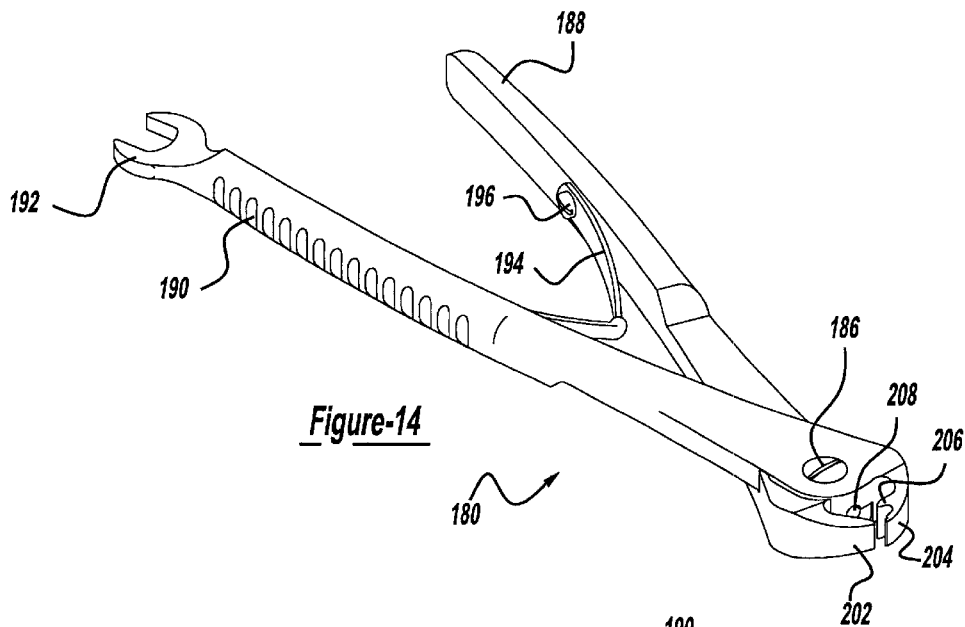
FIG. 14 is a perspective view of a cranial clamp post cutter instrument according to the teachings of the present invention.
Figure 15:
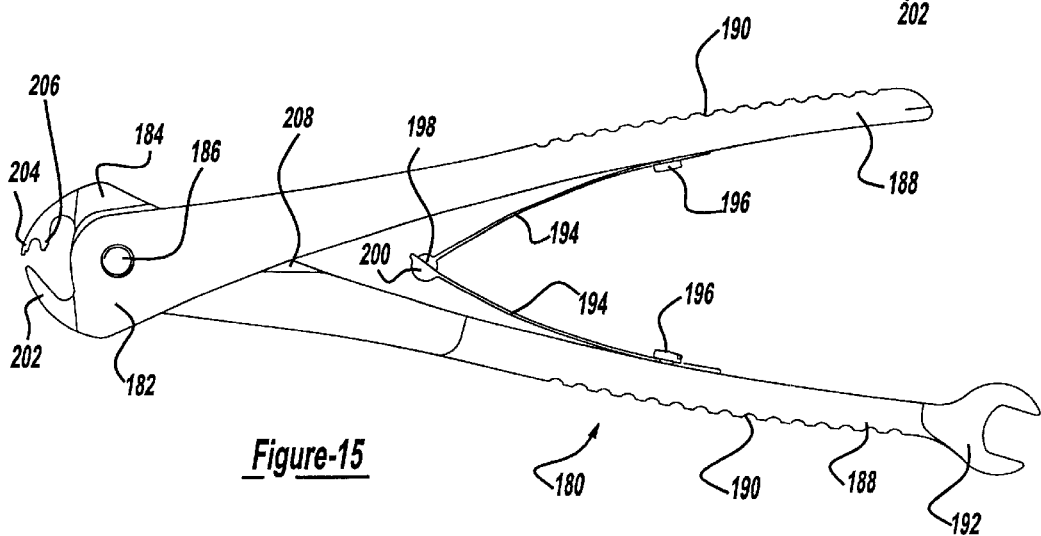
FIG. 15 is a side elevational view of the cranial clamp post cutter instrument of FIG. 14.
Figure 16:
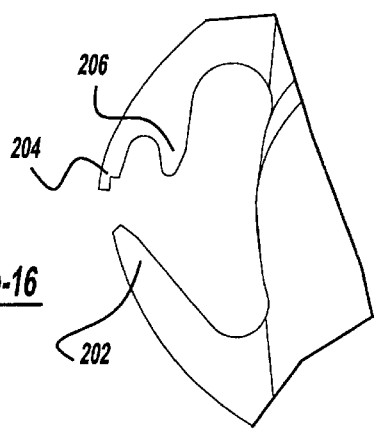
FIG. 16 is an enlarged view of a distal end of the cranial clamp post cutter instrument of FIG. 14.
Figure 17:
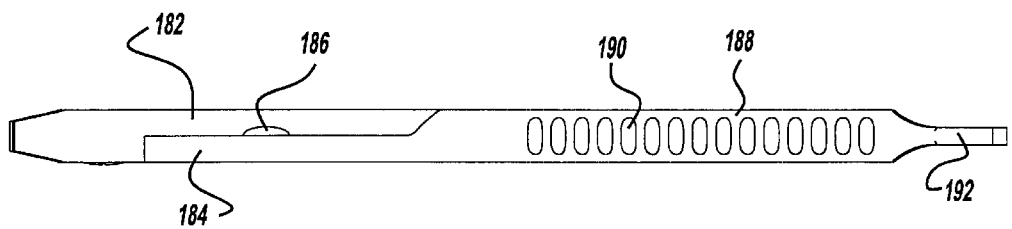
FIG. 17 is a bottom elevational view of the cranial clamp post cutter instrument of FIG. 14.

In use, the proximal end 28 of the stem 16 is slidably received through the bore 80 and positioned between the collets 132, as shown clearly in FIG. 9. With the trigger 76 fully opened, the linkage arms 108 and 110 forces the entire internal assembly 70 forward or distally. In this position, the spring 138 forces the two halves of the collets 132 distally into engagement with a conical separator 140 positioned concentrically about the bore 80 of the endcap 78. This conical separator 140 nestingly mates with the distal most end of the collets 132 to separate and open the collets 132 to expose a textured engagement surface or teeth 142.

The teeth 142 have a pitch and are appropriately spaced apart so that they correspondingly line up and nestingly mate or engage the textured engagement surface or annular ridges 34 on the stem 16. The textured engagement surfaces may be formed by the teeth 142 and the annular ridges 34 to reduce the overall grip strength required to move the cap 14 toward the base 12 or formed from any other appropriate textured engagement surfaces. In other words, since the stem 16 includes the annular ridges 34 and the collets 132 include the teeth 142, the strength of the engagement spring 138 may be substantially reduced by approximately one-half as compared to the use of a smooth cylindrical engagement stem 16. By reducing the strength of the compression spring 138, the springs 98 and 102 are likewise adjusted or reduced since these springs 98 and 102 are required to have the same spring force or strength as the spring 138. The mating textured engagement surfaces, therefore, reduces the required hand grip strength by one half, making the applier instrument 66 easier to operate and engage a cranial clamp 10.

With the stem 16 fully extended between the teeth 142 and the annular ledge 82 engaging the cap 14, the trigger 76 is then depressed. Upon squeezing the trigger 76, the collet tube 130 initially moves proximally which forces the collets 132 closed so that the teeth 142 nestingly engage the annular ridges 34 along the stem 16. This closing occurs as the collets 132 move proximally away from the conical separator 140. As the collets 132 and the tube 130 moves proximally, the spring 138 maintains a closure force on the collets 132 as they engage and grip the stem 16. This action draws the stem 16 into the bore 80 and compresses or moves the cap 14 closer to the base 12. Should the user continue to squeeze the trigger 76 beyond the maximum limiting force of about 110 lbs, the stack of Belleville washers 120 will compress along the shaft 122 as the Belleville tube 116 continues to move proximally. In other words, the shaft 122 and collets 132 substantially cease moving as the Belleville tube 116 continues to move proximally to compress the Belleville washers 120. This prevents further force being applied to the cap 14, thereby limiting the force applied to the cranial flap and the skull.

Once used, the applier instrument 66 is disassembled for cleaning and sterilization. In this regard, wrenches are used to engage the planar regions 86 of endcap 78 to remove the endcap 78 and the applier tube 72. Once removed, the inner assembly 70 is exposed. With the inner assembly 70 exposed, the collet tube 130 is removed upon holding the Belleville plunger 124, via the planar regions 128 with a wrench and rotating the collet tube 130 upon engaging the planar regions 144 with another wrench. Once disassembled, the applier tube 72, collet tube 130, collets 132 and spring 138 are cleaned and sterilized, as well as other components for subsequent use. By providing separate inner and outer assemblies 68 and 70, the applier instrument 66 may be easily disassembled and assembled for cleaning and sterilization operations within about one (1) minute. The components of the cranial clamp applier instrument 66 are preferably made from stainless steel or other appropriate material, while the collets 132 preferably have a chromium nitride coating to provide corrosion resistance and increased hardness in this area.

Referring now to FIGS. 10–13, a cranial clamp post or stem holder instrument 146 according to the teachings of the present invention is shown. The cranial clamp post holder instrument 146 is used to engage the post or stem 16 of the adjustable cranial clamp 10 as the applier instrument 66 forces the cap 14 downward adjacent to the cranial flap and skull, further discussed herein. The post holder instrument 146 includes a first half 148 and a second half 150 which pivot relative to one another about pivot point 152. Located at the proximal end of the post holder 146 are a pair of arcuate shaped handles 154 each including notches 156 to provide frictional engagement with a user's hand. Positioned at the distal end of the post holder 146 are a pair of angled engagement fingers 158, each having a straight abutment face 160 and an arcuate notch 162. The abutment faces 160 may have teeth or be planar.

Each arcuate notch 162 is sized to clampingly engage the rectangular annular ridge portion 32 of the stem 16. For example, if the stem 16 has an outer diameter of 0.060 inch, the hole formed by the arcuate notches 162 is sized to between about 0.048 inch and 0.056 inch to provide a sufficient compression or press fit about the stem 16. The abutment faces 160 prevent further engagement of the arcuate notches 162 about the stem 16 to inhibit or prevent notches being formed on the stem 16. In this regard, since the cranial clamp 10 is preferably formed from titanium or other biocompatible material, it may have a notch sensitivity to excessive external scarring on the stem 16 that may cause a weakening in this area. By limiting the engagement to a predetermined amount of engagement force, notch sensitivity is reduced.

The post holder instrument 146 further includes a spring lock mechanism 164. The spring lock mechanism 164 includes a pair of geared teeth 166 and a single engagement tooth 168. In use, the user simply squeezes the handles 154 once so that the tooth 168 is engaged between the teeth 166, along a ledge 170, shown in FIG. 13. To release the post holder instrument 146, the user simply squeezes the handles 154 once again to force the tooth 168 over the teeth 166 as it returns about a return area 172. In this way, a user simply squeezes once to retain the stem 16 and squeezes a subsequent time to release the stem 16. This provides for a one hand engagement and removal operation, as well as an ambidextrous type instrument. In this regard, a right or left handed user would be comfortable engaging and releasing the stem 16 with either the right or left hand, while using the applier instrument 166 in the opposite hand. The post holder instrument 146 also includes a spring 174 retained to the first half 148, via a screw 176, and slidably guided relative to the second half 150, via a pin 178. The post holder instrument 146 is preferably formed from stainless steel or other appropriate material.

Referring now to FIGS. 14–17, a cranial clamp post or stem cutter instrument 180 according to the teachings of the present invention is shown. The cranial clamp post cutter instrument 180 includes a cutter half 182 and an anvil half 184 which pivots about pivot point 186. Located at the proximal end of the post cutter instrument 180 are a pair of handles 188 each including a plurality of notches 190 to provide for frictional engagement of a user's hand. Located at the distal end of the anvil half 184 is an integral open end box wrench 192. The wrench 192 is operable to engage the planar regions 86, 128 and 144 of the applier instrument 66 for assembly and disassembly of the applier instrument 66 for cleaning and sterilization thereof. Secured to each of the handles 188 is a spring 194 which is secured to each handle 188 by way of a screw 196. Each spring 194 biases the post cutter instrument 180 in an open condition with the first spring 194 including a ball 198 and the second spring 194 including a socket 200.

Located at the distal end of the post cutter 180 is a cutter 202 and an anvil 204, that includes a stabilizing/bending arm 206. In this regard, the anvil 204 is offset from the cutter 202 to provide a shear force to shear the stem 14 which reduces or eliminates any sharp surfaces on the remaining stem portion. This is opposed to cutting where both cutting surfaces meet which generally creates sharp barbs on the remaining cut surface that could create abrasion at the scalp.

In use, the post cutter 180 is slid substantially perpendicular over the post or stem 16. The stem 16 passes between the cutter 202 and anvil 204 and is slidably received within a capture mechanism or groove 208 formed within each half 182 and 184. Upon depressing the handles 188, a three point stabilized contact is achieved along the stem 16 at the cutter 202, anvil 204 and stabilizing arm 206. Upon applying further force, the cutter 202 and anvil 204 shear the post or stem 16, while the stabilizing/bending arm 206 bends the remaining distal end of the cut stem 16. As the cutter 202 nests adjacent to the anvil 204, the remaining stem 16 is captured within the groove 208 while the bent end prevents it from sliding proximally out of the groove 208. Here again, the post cutter 180 is preferably formed from stainless steel or other appropriate materials.

Figure 18:
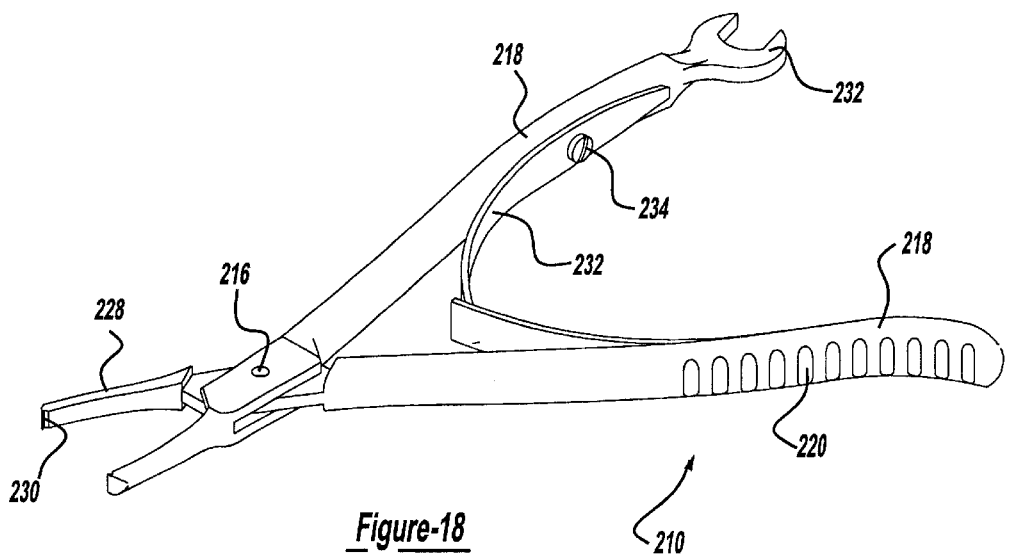
FIG. 18 is a perspective view of a cranial clamp removal forceps instrument according to the teachings of the present invention.
Figure 19:
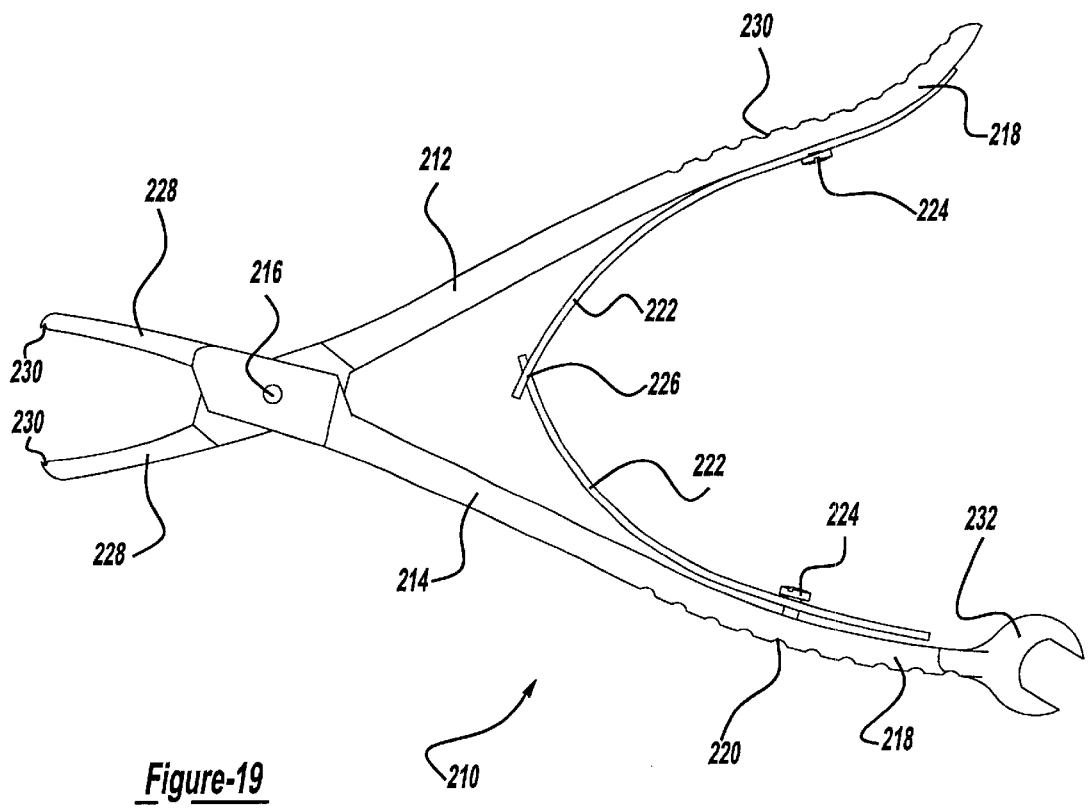
FIG. 19 is a side elevational view of the cranial clamp removal forceps instrument of FIG. 18.
Figure 20:
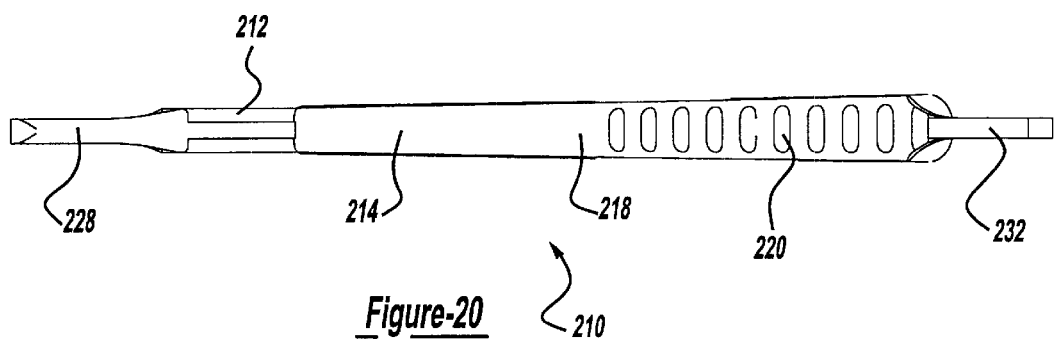
FIG. 20 is a bottom elevational view of the cranial clamp removal forceps instrument of FIG. 18.

Finally, referring to FIGS. 18–20, a plate removal forceps instrument 210 according to the teachings of the present invention is shown. The removal forceps instrument 210 is used to remove the cranial clamp 10 after it has been implanted should this be required. The plate removal forceps instrument 210 includes a first half 212 and a second half 214 which pivots about a pivot point 216. Located at the proximal end of the removal forceps instrument 210 are a pair of opposed arcuate handles 218, each including a plurality of notches 220 to frictionally engage a hand of the user. The handle 218 located on the first half 212 is curved away or outward from the forceps instrument 210, while the handle 218 on the second half 214 is curved toward the forceps instrument 210. This provides a better gripping capability for a user when removing the cap 14 relative to the stem 16. Each handle 218 also includes a spring 222 which is secured to each handle 218 by way of a screw 224. Each spring 222 engages one another at intersection 226 to bias the removal forceps instrument 210 in an opened condition. Located at the distal end of the forceps instrument 210 are a pair of arcuate fingers 228 each having a v-shaped notch 230.

In use, the v-shaped notches 230 are placed beneath the cap 14 so that the edge of the cap 14 fits within the notches 230. As the user firmly grips the handles 218, the user may then rock the removal forceps instrument 210 back until the cap 14 gives way from the stem 16. When this occurs, the cap 14 remains held by the forceps instrument 210 within the notches 230, thereby preventing the cap 14 from flying or projecting off the stem 16. The removal forceps instrument 210 also includes an integral open end box wrench 232 similar to the wrench 192 on the post cutter 180. Here again, the wrench 232 may be used in combination with the wrench 192 to assemble and disassemble the applier instrument 66 upon engaging the planar regions 86, 128 and 144.

Turning to FIGS. 21A–21F, a method of implanting the cranial clamp 10 using the above-identified set of instruments is illustrated. In order to gain access to the brain, one or more burr holes 228 are first drilled through the cranium or skull 230 of the patient. These burr holes 228 may be arranged in many different shapes such as a triangle, as shown, or any other required shape. Slots 232 are then cut between the burr holes 228 to form a cranial flap or cover 234. The bone flap 234 may then be removed to expose the dura matter of the patient. Once surgery has been completed on the patient, the bone flap 234 is required to be secured relative to the skull 230.

Figure 21A:
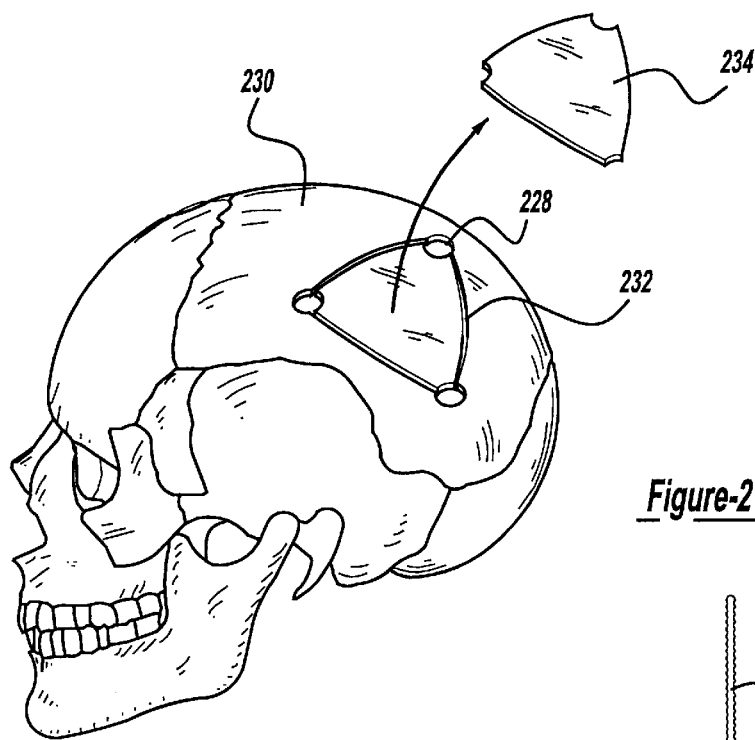
FIGS. 21A–21F illustrates a method of implanting the cranial clamp using the above shown set of instruments according to the teachings of the present invention.
Figure 21B:
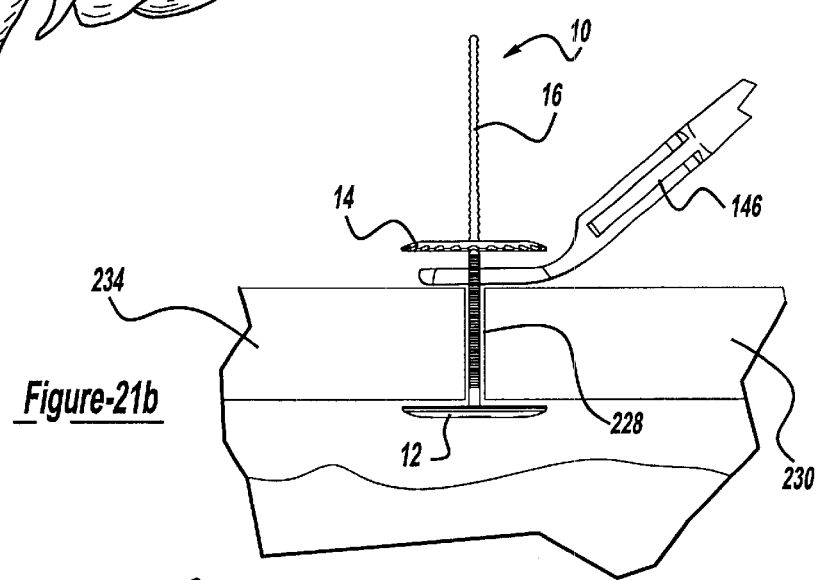

Prior to fitting the bone flap 234 within the skull 230, three (3) cranial clamps 10 are laid adjacent each burr hole 228. The bone flap 234 is then positioned between the base 12 and the cap 14 of each cranial clamp 10, as shown in FIG. 21B. The arcuate notches 162 of the cranial clamp post holder instrument 146 are locked about a stem 16 of one of the cranial clamps 10. Upon engaging the handles 154, the tooth 168 is engaged within the teeth 166 and comes to rest within ledge 170. The post holder instrument 146 assures that the base 12 is not forced downward atop the dura matter upon using the applier instrument 66 to move the cap 14 adjacent to the base 12.

Figure 21C:
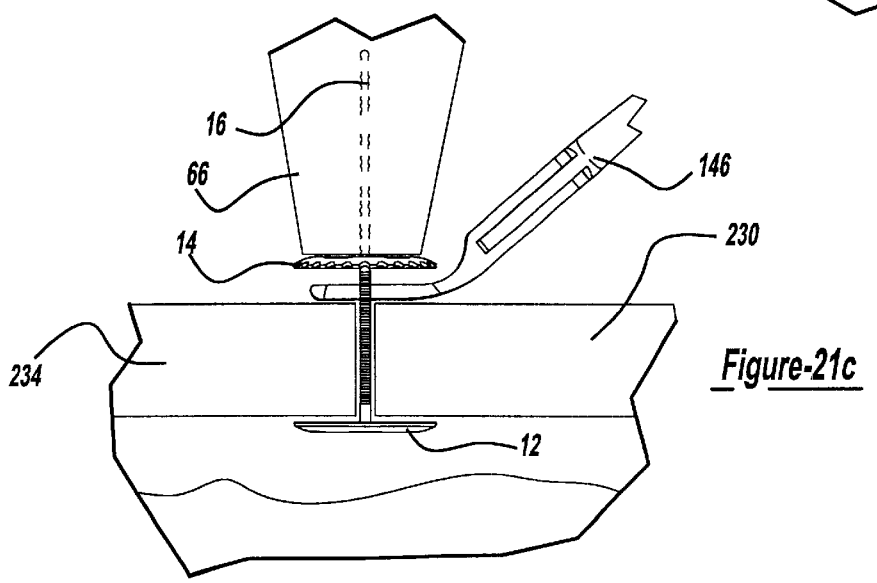

Once the post holder instrument 146 is secured about the post or stem 16, the applier instrument 66 is slid over the proximal end of the stem 16. As shown in FIG. 21C, a sectional view of the base 12, bone flap 234, skull 230, post holder instrument 146, cap 14 and applier instrument 66 are shown. With the stem or post 16 firmly gripped by the post holder 146, the surgeon or user will grip the trigger 76 of the applier instrument 66 to compress and force the cap 14 to move towards the base 12 of the cranial clamp 10.

Figure 21D:
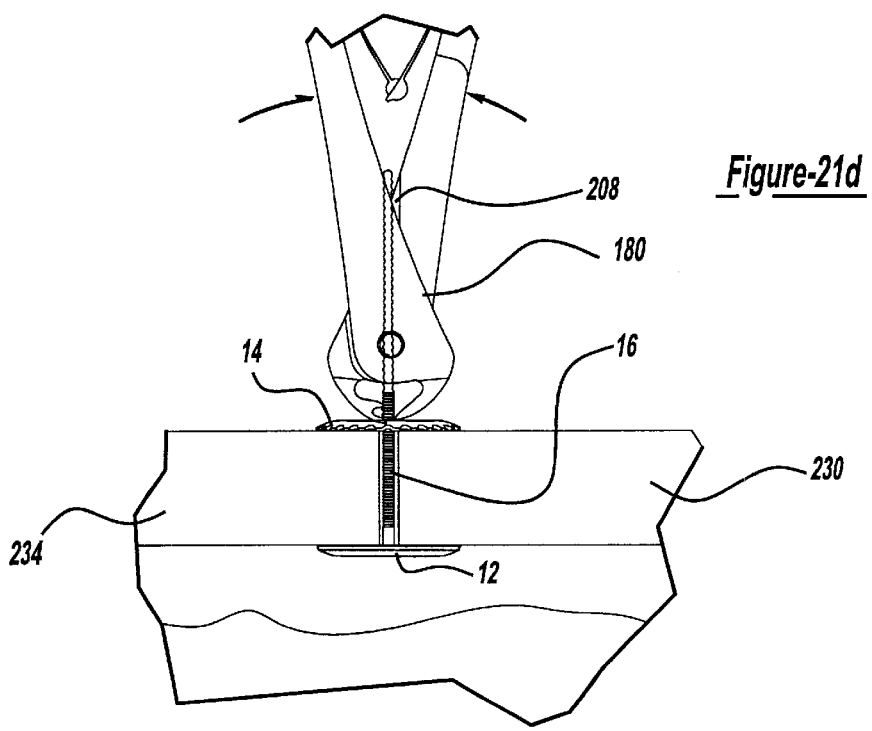
Figure 21E:
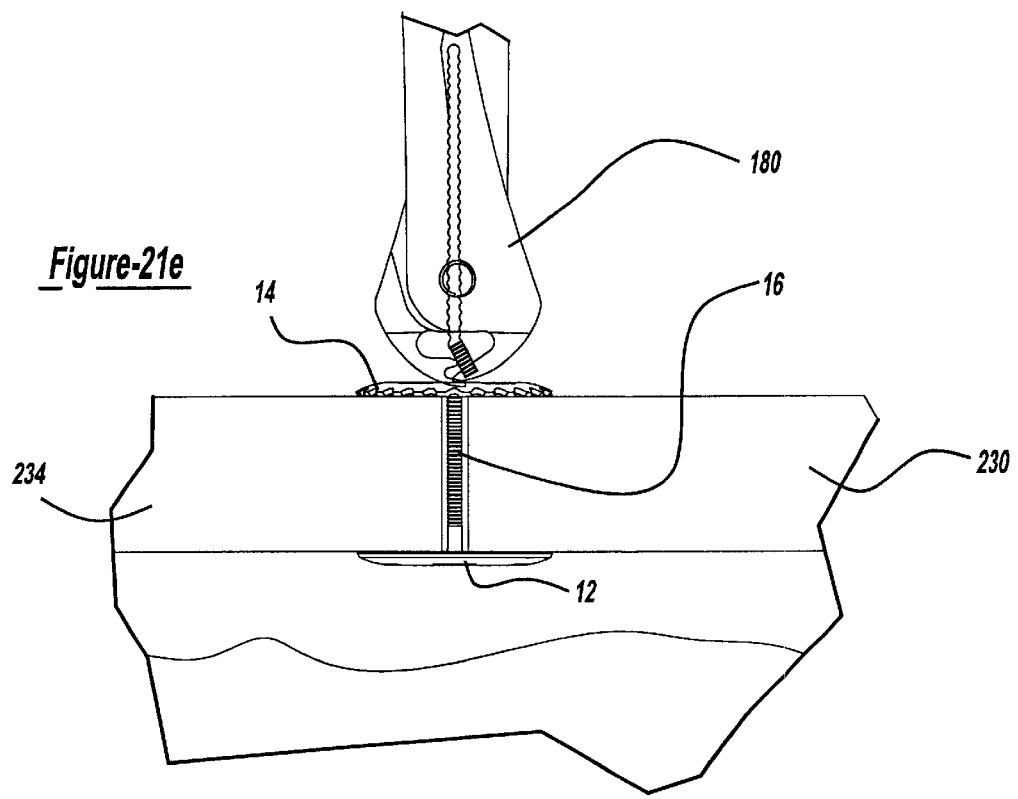
Figure 21F:
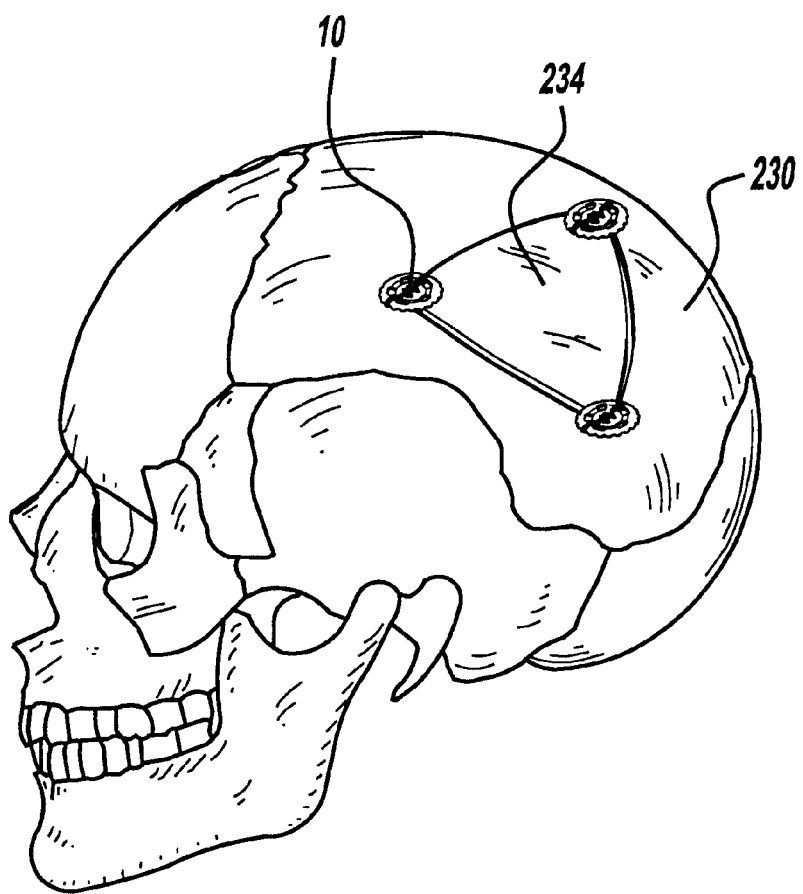

Upon seating or moving the cap 14 adjacent to the post holder instrument 146, the post holder instrument 146 is removed from the stem 16 and the applier instrument 66 is again actuated to snuggly engage the cap 14 relative to the outer surface of the bone flap 234 and the skull 230. Once the cap 14 is snuggly engaged against the bone flap 234 and the skull or cranium 230, the applier instrument 66 is disengaged and removed from the stem 16. This technique is then performed on each cranial clamp 10. The post cutter instrument 180 is then used to cut the excess portion of the stem 16 extending out beyond each cap 14, as shown in FIGS. 21D and 21E. In this regard, the stem 16 is sheared by the cutter 202 and anvil 204, while the stabilizing/bending arm 206 bends the distal end of the remaining portion of the stem 16 to hold and capture it within the groove 208. The fully secured cranial flap 234 is shown in FIG. 21F.

By use of the adjustable cranial clamp 10 and the set of instruments set forth above, an efficient and secure manner of fixing the cranial flap 234 relative to the skull 230 is shown. The cranial clamp 10 provides improved retaining, as well as pull-off strength based upon the configuration of the resilient fingers 54. The cranial clamp 10 further is manufactured in an efficient cost effective manner by using the larger circular cutter 62. The set of instruments may be used by either right or left hand users, thereby eliminating a need for different sets of instruments depending on the user. This set of instruments also reduces the amount of grip strength required to compress the cap 14 relative to the base 12, eliminates sharp edges on the stem 16 upon cutting the stem, provides a predetermined amount of grip strength about the holding stem 16 to reduce or eliminate notch sensitivity, and eliminates the cut portion of the stem 16 or the cap 14 from being displaced upon their removal. Finally, use of the integral wrenches also reduces the number of surgical instruments required, as well as provides a larger instrument to maneuver the wrenches to disassemble and sterilize the applier instrument 66.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention.

What is claimed is:

1. A set of surgical instruments for use in reattachment of a cranial flap using a cranial clamp having a base, a cap and a stem, said set of surgical instruments comprising:

an applier instrument operable to slidably receive a portion of the stem and operable to move the cap relative to the base; and a stem cutter instrument operable to remove a portion of the stem from the cranial clamp, said stem cutter instrument including a capture mechanism operable to retain a removed portion of the stem, wherein said set of surgical instruments is used to implant the cranial clamp to reattach the cranial flap.

2. The set of surgical instruments as defined in claim 1 wherein said applier instrument further includes an engagement mechanism having a textured engagement surface that matingly engages a textured engagement surface on a portion of the stem.

3. The set of surgical instruments as defined in claim 2 wherein said mating textured engagement surfaces are formed by a plurality of annular ridges on the stem and a plurality of corresponding mating teeth on said engagement mechanism.

4. The set of surgical instruments as defined in claim 1 wherein said barrel is angled downward toward said trigger.

5. The set of surgical instruments as defined in claim 1 wherein said applier instrument further includes a force limiting mechanism operable to limit an amount of force applied to the cap.

6. The set of surgical instruments as defined in claim 1 further comprising a stem holder instrument operable to engage and hold a portion of the stem.

7. The set of surgical instruments as defined in claim 6 wherein said stem holder instrument includes a pair of handles and a lock mechanism operable to be locked upon squeezing said pair of handles once and operable to be opened upon squeezing said pair of handles once again.

8. The set of surgical instruments as defined in claim 1 further comprising a stem holder instrument operable to engage and hold a portion of the stem and a removal forceps operable to remove the cap from the cranial cramp.

9. The set of surgical instruments as defined in claim 6 wherein said stem holder instrument includes a pair of handles and a lock mechanism operable to lock said pair of handles.

10. The set of surgical instruments as defined in claim 9 wherein said lock mechanism is operable to be locked upon squeezing said pair of handles once and operable to be opened upon squeezing said pair of handles once again.

11. The set of surgical instruments as defined in claim 10 wherein said lock mechanism includes a pair of teeth and a single tooth that engages said teeth.

12. The set of surgical instruments as defined in claim 7 wherein said removal forceps include an engagement region operable to engage and retain the cap upon its removal from the cranial clamp.

13. The set of surgical instruments as defined in claim 7 wherein said removal forceps include a pair of handles and a spring mechanism operable to bias the removal forceps in an opened condition.

14. The set of surgical instruments as defined in claim 1 wherein said applier instrument includes an engagement mechanism having a textured engagement surface that engages a textured engagement surface on a portion of the stem.

15. The set of surgical instruments as defined in claim 14 wherein said applier instrument further includes a force limiting mechanism operable to limit an amount of force applied to the cap.

16. The set of surgical instruments as defined in claim 14 wherein said textured engagement surfaces are formed by a plurality of annular ridges on the stem and a plurality of corresponding mating teeth on said engagement mechanism.

17. The set of surgical instruments as defined in claim 1 wherein said stem cutter instrument includes a cutter operable to cut a portion of the stem.

18. A set of surgical instruments for use in reattachment of a cranial flap using a cranial clamp having a base, a cap and a stern, said set of surgical instruments comprising:
an applier instrument operable to slidably receive a portion of the stern and operable to move the cap relative to the base, said applier instrument including a handle, a trigger and a barrel configured as a gun-style instrument; and
a stem cutter instrument operable to remove a portion of the stem from the cranial clamp, said stem cutter instrument includes a capture mechanism operable to retain a sheared portion of the stem, wherein said set of surgical instruments is used to implant the cranial clamp to reattach the cranial flap.

19. The set of surgical instruments as defined in claim 18 wherein said applier instrument further includes an engagement mechanism having a textured engagement surface that matingly engages a textured engagement surface on a portion of the stem.

20. The set of surgical instruments as defined in claim 19 wherein said stem cutter instrument further includes an extension member adjacent said anvil for bending a portion of said sheared portion of the stem.

21. The set of surgical instruments as defined in claim 18 wherein said barrel is angled downward toward said trigger.

22. The set of surgical instruments as defined in claim 18 wherein said applier instrument further includes a force limiting mechanism operable to limit an amount of force applied to the cap.

23. The set of surgical instruments as defined in claim 18 further comprising a stern holder instrument operable to engage and hold a portion of the stem.

24. A method of reattachment of a cranial flap using a cranial clamp having a base, a cap and a stem, said method comprising:
engaging a textured surface on a portion of the stem with an applier instrument having a mating textured surface;
moving the cap relative to the base as the applier instrument matingly engages the textured surface on the portion of the stem; and
removing a portion of the stem from the cranial clamp with a stem cutter instrument.

25. The set of surgical instruments as defined in claim 18 further comprising a removal forceps instrument operable to remove the cap from the cranial clamp, said removal forceps instrument including an engagement region operable to engage and retain the cap upon its removal from the cranial clamp.

26. The set of surgical instruments as defined in claim 25 wherein said removal forceps instrument further includes an integral wrench operable to be used in the assembly and disassembly of said applier instrument.

27. A set of surgical instruments for use in reattachment of a cranial flap using a cranial clamp having a base, a cap and a stem, said set of surgical instruments comprising:
an applier instrument operable to slidably receive a portion of the stem and operable to move the cap relative to the base, said applier instrument including an engagement mechanism having a textured engagement surface that matingly engages a texture engagement surface on a portion of the stem, said applier instrument configured as a gun-style instrument having a handle, a trigger and a barrel; and
a stem cutter instrument operable to remove a portion of the stem from the cranial clamp, said stem cutter instrument includes a capture mechanism operable to retain a sheared portion of the stem, wherein said set of surgical instruments is used to implant the cranial clamp to reattach the cranial flap.

28. The set of surgical instruments as defined in claim 27 wherein said mating textured engagement surfaces are formed by a plurality of annular ridges on the stem and a plurality of corresponding mating teeth on said engagement mechanism.

29. The set of surgical instruments as defined in claim 27 further comprising a stem holder instrument operable to engage and hold a portion of the stem, said stem holder instrument includes a pair of handles and a lock mechanism operable to be locked upon squeezing said pair of handles once and operable to be opened upon squeezing said pair of handles once again.

30. A set of surgical instruments for use in reattachment of a cranial flap using a cranial clamp having a base, a cap and a stern, said set of surgical instruments comprising:
an applier instrument operable to slidably receive a portion of the stem and operable to move the cap relative to the base;
a stem holder instrument operable to engage and hold a portion of the stem, said stem holder instrument including a pair of handles and a lock mechanism operable to be locked upon squeezing said pair of handles once and operable to be opened upon squeezing said pair of handles once again, said lock mechanism includes a pair of teeth and a single tooth that engages said teeth; and a stem cutter instrument operable to remove a portion of the stem from the cranial clamp, wherein said set of surgical instruments is used to implant the cranial clamp to reattach the cranial flap.

31. The set of surgical instruments as defined in claim 30 further comprising a removal forceps operable to remove the cap from the cranial clamp.

32. The ste of surgical instruments as defined in claim 31 wherein said removal forceps include an engagement region operable to engage and retain the cap upon its removal from the cranial clamp.

33. The set of surgical instruments as defined in claim 31 wherein said removal forceps include a pair of handles and a spring mechanism operable to bias the removal forceps in an opened condition.

34. The set of surgical instruments as defined in claim 30 wherein said applier instrument includes an engagement mechanism having a textured engagement surface that engages a textured engagement surface on a portion of the stem.

35. The set of surgical instruments as defined in claim 34 wherein said applier instrument further includes a force limiting mechanism operable to limit an amount of force applied to the cap.

36. The set of surgical instruments as defined in claim 30 wherein said stem cutter instrument includes an anvil and a cutter operable to shear a portion of the stem.

37. The set of surgical instruments as defined in claim 36 wherein said stem cutter instrument further includes an extension member adjacent said anvil for bend a portion of said sheared portion of the stem.

38. The set of surgical instruments as defined in claim 37 wherein said capture mechanism is defined by a groove.

39. The set of surgical instruments as defined in claim 30 wherein said stem cutter instrument includes a cutter operable to cut a portion of the stem.

* * * * *

UNITED STATES PATENT AND TRADEMARK OFFICE
CERTIFICATE OF CORRECTION

PATENT NO.    : 6,379,363 B1
DATED         : April 30, 2002
INVENTOR(S)   : Herrington et al.

It is certified that error appears in the above-identified patent and that said Letters Patent is hereby corrected as shown below:

<u>Title page,</u>
Item [56], References Cited, FOREIGN PATENT DOCUMENTS, "296 14 293" should be -- 296 14 923 --;
OTHER PUBLICATIONS,
"Gmbh" should be -- GmbH --; and
insert -- Aesculap CranioFIX Titanium Clamp Instruction Manual (28 sheets) in various languages, dated 01/99 --.

<u>Column 2,</u>
Line 7, "instruments" should be -- instrument --.

<u>Column 3,</u>
Line 60, "illustrates" should be -- illustrate --.

<u>Column 10, line 49 through Column 11, line 5,</u>
Delete Claims 2 through 7 and insert:

-- 2.   The set of surgical instruments as defined in Claim 1 wherein said stem cutter instrument includes an anvil and a cutter operable to shear a portion of the stem.

3.   The set of surgical instruments as defined in Claim 2 wherein said stem cutter instrument further includes an extension member adjacent said anvil for bending a portion of said sheared portion of the stem.

4.   The set of surgical instruments as defined in Claim 3 wherein said capture mechanism is defined by a groove.

5.   The set of surgical instruments as defined in Claim 5 wherein said stem cutter instrument further includes an integral wrench operable to be used in the assembly and disassembly of said applier instrument.

6.   The set of surgical instruments as defined in Claim 1 further comprising a stem holder instrument operable to engage and hold a portion of the stem.

7.   The set of surgical instruments as defined in Claim 1 further comprising a removal forceps operable to remove the cap from the cranial clamp. --.

UNITED STATES PATENT AND TRADEMARK OFFICE
CERTIFICATE OF CORRECTION

PATENT NO. : 6,379,363 B1
DATED : April 30, 2002
INVENTOR(S) : Herrington et al.

It is certified that error appears in the above-identified patent and that said Letters Patent is hereby corrected as shown below:

Column 11,
Lines 47 and 49, "stern" should be -- stem --.
Lines 64-67, delete Claim 20 and insert:
-- 20. The set of surgical instruments as defined in Claim 19 wherein said mating textured engagement surfaces are formed by a plurality of annular ridges on the stem and a plurality of corresponding mating teeth on said engagement mechanism. --.

Column 12,
Lines 8 and 62, "stern" should be -- stem --.
Lines 10-19, delete Claim 24 and insert:
-- 24. The set of surgical instruments as defined in Claim 23 wherein said stem holder instrument includes a pair of handles and a lock mechanism operable to be locked upon squeezing said pair of handles once and operable to be opened upon squeezing said pair of handles once again. --.

Column 13,
Line 14, "ste" should be -- set --.

Column 14,
Line 15, "bend" should be -- bending --.

Signed and Sealed this

Twenty-eighth Day of February, 2006

JON W. DUDAS
*Director of the United States Patent and Trademark Office*